(12) United States Patent
Bode et al.

(10) Patent No.: US 9,111,404 B2
(45) Date of Patent: Aug. 18, 2015

(54) VENDING APPARATUS AND METHOD FOR PROVIDING TRAINING FOR A MEDICINAL PRODUCT OR MEDICAL DEVICE OR COMBINATION PRODUCT

(75) Inventors: Andreas Bode, Frankfurt am Main (DE); Serpil Heger, Frankfurt am Main (DE); Laurin Stroessenreuther, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 328 days.

(21) Appl. No.: 13/637,660

(22) PCT Filed: Mar. 31, 2011

(86) PCT No.: PCT/EP2011/054983
§ 371 (c)(1),
(2), (4) Date: Mar. 21, 2013

(87) PCT Pub. No.: WO2011/121059
PCT Pub. Date: Oct. 6, 2011

(65) Prior Publication Data
US 2013/0197692 A1  Aug. 1, 2013

(30) Foreign Application Priority Data
Mar. 31, 2010 (EP) .................................. 10158558

(51) Int. Cl.
*G07F 9/00* (2006.01)
*G07F 9/02* (2006.01)
(Continued)

(52) U.S. Cl.
CPC .............. *G07F 9/00* (2013.01); *G06F 19/3462* (2013.01); *G07F 9/02* (2013.01); *G07F 17/0092* (2013.01)

(58) Field of Classification Search
CPC ............................... G07F 17/0092; A61J 7/04
USPC ......................................................... 700/237
See application file for complete search history.

(56) References Cited

U.S. PATENT DOCUMENTS 6,892,941 B2 * 5/2005 Rosenblum ................... 700/237
7,783,378 B2 * 8/2010 Pinney et al. ................. 700/237
(Continued)

FOREIGN PATENT DOCUMENTS

JP      H0724044 A      1/1995
JP      2001052064 A    2/2001
(Continued)

OTHER PUBLICATIONS

European Search Report for European App. No. 10158558, completed Aug. 23, 2010.
(Continued)

*Primary Examiner* — Timothy Waggoner
(74) *Attorney, Agent, or Firm* — McDonnell Boehnen Hulbert & Berghoff LLP

(57) ABSTRACT

The present invention relates to a vending apparatus for at least one medicinal product, comprising of a housing, storage means adapted to store the at least one medicinal product, an input means adapted to process a costumer request for a medicinal product, processing means adapted to process the costumer request and being adapted to execute an interactive product-related training procedure to the customer, and delivery means for handing out the medicinal product to the costumer after passing the training procedure, wherein access to the medicinal product is only approved by the processing means if the customer successfully passes the training procedure.

10 Claims, 3 Drawing Sheets

(51) Int. Cl.
*G07F 17/00* (2006.01)
*G06F 19/00* (2011.01)

(56) References Cited

U.S. PATENT DOCUMENTS

| 8,738,177 | B2* | 5/2014 | van Ooyen et al. | 700/242 |
|---|---|---|---|---|
| 2002/0032582 | A1 | 3/2002 | Feeney, Jr. et al. | |
| 2002/0065579 | A1 | 5/2002 | Tedesco et al. | |
| 2004/0121295 | A1* | 6/2004 | Stuart et al. | 434/262 |
| 2005/0187656 | A1 | 8/2005 | Walker et al. | |
| 2011/0133948 | A1* | 6/2011 | Ervin | 700/237 |
| 2011/0245967 | A1* | 10/2011 | Shah et al. | 700/236 |

FOREIGN PATENT DOCUMENTS

| JP | 2009211314 A | 9/2009 |
|---|---|---|
| WO | 01/43088 | 6/2001 |

OTHER PUBLICATIONS

International Preliminary Report on Patentability for Int. App. No. PCT/EP2011/054983, mailed Jul. 11, 2012.
International Search Report for Int. App. No. PCT/EP2011/054983, completed Apr. 12, 2011.
English Abstract and English Language Translation of Japanese Patent Application No. JP 2001-052064.
English Abstract and English Language Translation of Japanese Patent Application No. JP 2009-211314.
English Abstract and English Language Translation of Japanese Patent No. H0724044.

* cited by examiner

VENDING APPARATUS AND METHOD FOR PROVIDING TRAINING FOR A MEDICINAL PRODUCT OR MEDICAL DEVICE OR COMBINATION PRODUCT

CROSS REFERENCE TO RELATED APPLICATIONS

The present application is a U.S. National Phase Application pursuant to 35 U.S.C. §371 of International Application No. PCT/EP2011/054983 filed Mar. 31, 2011, which claims priority to European Patent Application No. 10158558.6 filed on Mar. 31, 2010. The entire disclosure contents of these applications are herewith incorporated by reference into the present application.

FIELD OF THE INVENTION

The present invention relates to the field of authorized and controlled vending of medicinal products including training, in particular of drugs and/or medical devices to customers.

BACKGROUND

Home treatment for temporal or chronic diseases typically requires regular prescription and purchasing of at least one particular drug. Some drugs, like those that have to be administered subcutaneously or even intravenously additionally require respective training of the patient himself or of respective nursing staff.

However, in circumstances, where the drug to be administered temporally changes, the patient has to be repeatedly instructed on the proper use of the drug and/or on some drug-specific drug delivery device. In particular in terms of drug delivery devices even skilled medicinal personal, like doctors or pharmacists may be unfamiliar with its proper handling and usage. Additionally, the initial training given to a patient by a doctor, a pharmacist or comparable medical professional is quite often conducted in hectic atmosphere. Moreover, initial training for home medication is typically executed at the end of long-term stationary care in a hospital. At home, the patient finds himself in a different environment, which e.g. may confront him with further practical problems for self-administering the particular medicinal product.

There exists therefore a need for high-qualitative and regular patient training for the proper use of medicinal product and/or devices adapted to administer such products.

It is therefore an object of the present invention to provide a user-friendly, high-quality training for drugs and drug delivery devices that are utilized in a home treatment environment. It is a further object of the present invention, to reduce packing- and vending costs for medicinal products and corresponding drug delivery devices. Moreover, by way of the invention, delivery or availability and shelf-storage of medicinal products and related drug delivery devices should be enhanced.

SUMMARY

In a first aspect, the present invention relates to a vending apparatus for at least one medicinal product. The apparatus comprises a housing and storage means adapted to store the at least one medicinal product in appropriate conditions, e.g. stored at specific temperature ranges, e.g. cooled. The apparatus further comprises an input means adapted to process a customer request related to a particular medicinal product and further comprises processing means that are adapted to process the costumer request and which is further adapted to execute a product-related training procedure with the customer. The apparatus further comprises delivery means for handing out the requested medicinal product to the customer only if the customer has successfully passed the training procedure.

Depending on the type of requested medicinal product, the processing means may selectively modify the conditions under which access to a requested medicinal product is provided. For instance, if the requested medicinal product is prescription-free, the training procedure might be reduced to a simple illustration of the proper use of the medicinal product. Delivery of the medicinal product to the customer then does not require any further action of the customer. Hence, a threshold for passing the training procedure is substantially decreased.

Typically, the vending apparatus is adapted to give access to medicinal products and drugs. In this case the interactive product-related training procedure may in a first stage inform the customer about the recommended and preferred use of the medicinal product. Thereafter, in a second stage, the customer has to answer some product-specific question thereby proving a required minimum of appropriate product-related skills and knowledge. Consequently, access to the medicinal produced will only be approved if the customer successfully passes the training procedure executed by the processing means.

For instance, the training procedure comprises numerous arbitrarily selected multiple choice questions related to the product and/or the medical device. Depending on the requested product or medical device the level of passing the training procedure may vary. Moreover, also depending on side effects of the product and its risk to health upon improper administering, the percentage of correctly answered questions required in order to pass the training procedure may be lowered or raised, respectively.

The vending apparatus according to the present invention can be universally applied for vending medicinal products and related drug delivery devices as well as for providing product- or device-related information to the customer. By installing such vending apparatuses in public places, unlimited availability of the medicinal products and devices contained in the vending apparatus can be provided even outside the opening hours of pharmacies. Hence, by means of such vending apparatuses, a reliable and safe, fully automatic pharmaceutical product supply can be established.

In a further aspect, the apparatus comprises an authorization module for checking the identity of the customer and/or its authorization to receive the requested medicinal product. For instance, the customer may insert a customer-specific card into a card slot of the vending apparatus. The card itself can for instance be programmed by authorized medicinal staff. The card reader of the vending apparatus then reads the preferably encoded product-related information and automatically selects and delivers the requested drug. In this way it can be guaranteed, that the customer exactly receives the particular drug that has been prescribed by a doctor.

Additionally, if the apparatus is further supplied with a communication unit, the apparatus may further conduct a data cross check with a central database, in which the patient and patient-related drugs are listed. By means of a data cross check, also overdose application of the requested medicinal product could be easily identified and delivery of the product could be hindered.

Alternatively or additionally, the communication interface is adapted to communicate with a product-supply entity. If for instance the storage means is running short with respect to a particular medicinal product, by way of the communication interface, the apparatus may autonomously send a respective request for re-fill to the product-supply entity.

In a further preferred embodiment, the apparatus also comprises a leaflet printing module for printing of a customer-specific product-related leaflet. Additionally, the apparatus may comprise a language selection for the customer. Depending on the customer's language choice, a respective single-language leaflet for the respective medicinal product is generated on-site. Additionally, the apparatus may comprise a packaging unit, adapted to combine the product-specific leaflet with the associated product before the product-leaflet entity is delivered to the customer. By printing the drug-specific leaflet in the apparatus, packaging and printing costs for leaflets can be minimized.

Further, instead of multilingual leaflets, now a single and a user-specific leaflet can be generated and provided to the user. Also, it is conceivable, that the apparatus generates printed user-information on demand. Additional to the illustrated training procedure, the customer may prefer to read respective product-specific information in a printed version. In this case, the customer may simply request for printed product or device information.

In a further aspect, the input means of the apparatus comprises a touch-screen display, a keypad and/or a speech dialog system. Hence, the apparatus comprises input and output means that are adapted to visually and/or audibly communicate with the customer. In particular for customers having an impaired vision, a voice control of the apparatus is of major benefit.

In a further independent aspect, the present invention also relates to a method of vending at least one medicinal product by means of an above illustrated apparatus. Said method comprises the steps of processing a customer request for a medicinal product and selecting a product-related training procedure to be at least displayed or illustrated to the customer. In a final step, the requested product or device is delivered or handed out to the customer after execution of the training procedure.

Generally, access to the product and handing out of the product to the customer is only performed if the customer has successfully passed the training procedure. In this embodiment, the training procedure is of interactive type, wherein the customer has to answer a set of product-related questions. Hence, the customer has to prove that he has appropriate skills and knowledge about the respective drug and/or its corresponding drug delivery device.

Preferably, in further embodiments, the identity of the customer and/or its authorization to receive the requested medicinal product and/or a respective drug delivery device is checked prior to execution of the training procedure. For this purpose, a customer may have to insert a customer-related authorization card, e.g. in a card-reading slot of the vending apparatus. Data being stored on said card is preferably encrypted or encoded and may be manipulated only by authorized medicinal personnel, like a doctor. Upon reading of said encrypted information, the vending apparatus may grant or deny access to the medicinal product or device requested by the customer.

In a further preferred embodiment, a product-related leaflet is printed on-site e.g. in response to a language selection of the customer. In this way, packaging costs and packaging expenditure can be reduced to a minimum. The medicinal product or its related drug delivery device then only has to be supplied with a single-language leaflet, wherein assembling or packaging of leaflet and device can also be automatically conducted by way of the vending apparatus.

In a further independent aspect, the present invention also relates to a computer program product for operating the above-described vending apparatus. The computer program product comprises computer program means for processing a customer request for a medicinal product. The computer program product further comprises program means for selecting a product-related training procedure and for executing said training procedure with the customer. Finally, the computer program product also has program means for providing access to the product and for handing out the product to the customer only if the customer has successfully passed the training procedure.

It will be apparent to those skilled in the art that various modifications and variations can be made to the present invention without departing from its spirit and scope. Further, it is to be noted, that any reference signs used in the appended claims are not to be construed as limiting the scope of the present invention.

BRIEF DESCRIPTION OF THE DRAWINGS

Without limitation, the present invention will be explained in greater detail below in connection with preferred embodiments and with reference to the drawings in which.

DETAILED DESCRIPTION

Figure 1:
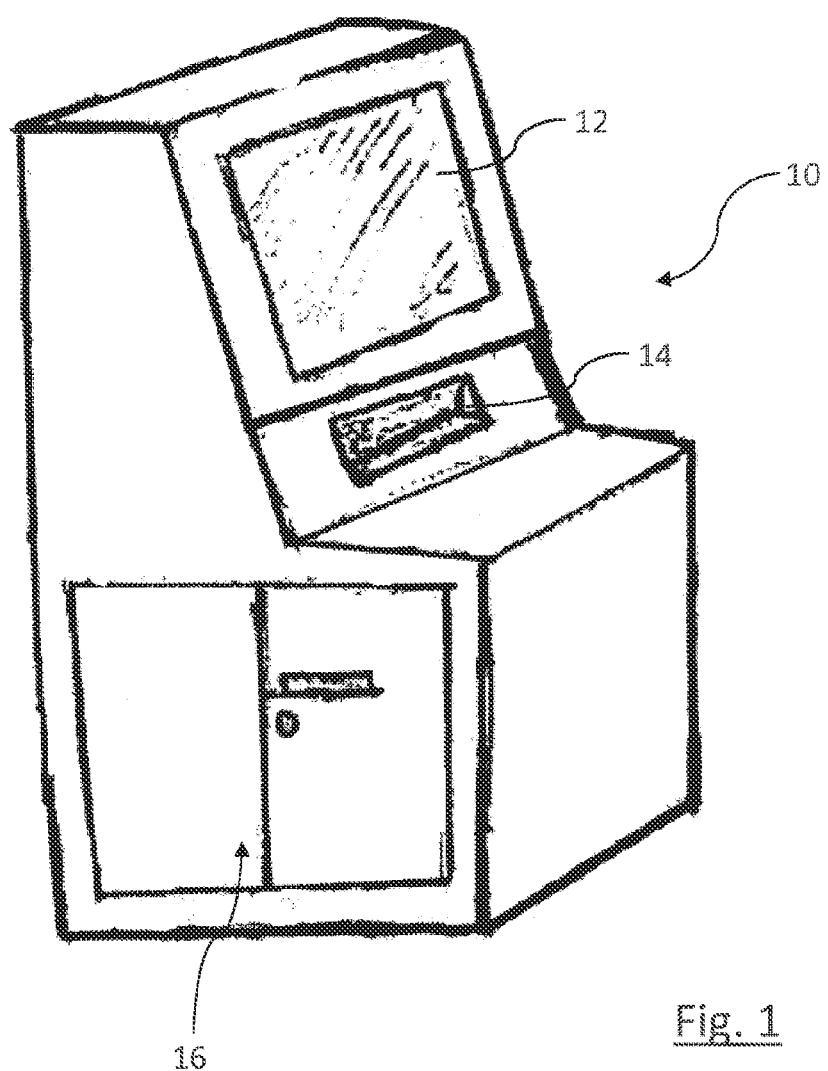
FIG. 1 schematically illustrates a vending apparatus according to the present invention.

The vending apparatus 10 according to FIG. 1 comprises a storage means 16 for storing at least one medicinal product and/or at least one corresponding medical devices at appropriate environmental conditions. The vending apparatus 10 further has input and display means 12, e.g. in form of a touchscreen. By way of such in- and output means 12, a customer may enter a customer request and may then be provided with product-related facts and information.

Moreover, the combined input- and display means 12 is adapted to execute an interactive training procedure with the customer. In a first stage for instance, the display means 12 may illustrate product-related facts and information and in a second stage, the customer has to pass an examination or test procedure, typically, by answering numerous multiple choice questions, thereby proving, that he has basic and substantial knowledge on the proper treatment and application of the requested product or the requested device. If the customer has passed the interactive training procedure, the medicinal product and/or the respective medical device is handed out to the customer by way of a delivery module 14, which may be designed as an output slot.

The vending apparatus 10 further comprises a storage module 16, which, depending on the type of medicinal product to be distributed may also provide a refrigerating function. In this way, the medicinal product is kept at optimal environmental conditions. If for instance the vending apparatus is adapted to distribute drugs requiring constant refrigeration, such like insulin, heparin or erythropoietin (EPO), establishment of a required cold chain in the customer supply chain can be easily provided.

Depending on the type of medicinal product requested by the customer, the training procedure may vary. For instance for prescription-free products, where even a misuse may not endanger the customer's health, the training procedure may be limited to a mere illustration of product-related information.

However, if the requested product might be harmful to health if not properly administered, the requested medicinal product or device will only be handed out to the customer if the product-related training procedure has been successfully passed by the customer.

Another benefit to be achieved with the vending apparatus 10 is a reduction in packaging and printing expenditure. Since the customer may select a preferred language when requesting the product or device, the vending apparatus may individually print a respective product-related leaflet, which is to be handed out to the customer together with the respective product or device. In this way, printing and packaging of multilingual leaflets and packages can be obviated. Moreover, the customer may even specify whether a detailed leaflet with extensive explanation or a short version of a leaflet has to be printed and handed out.

Figure 2:
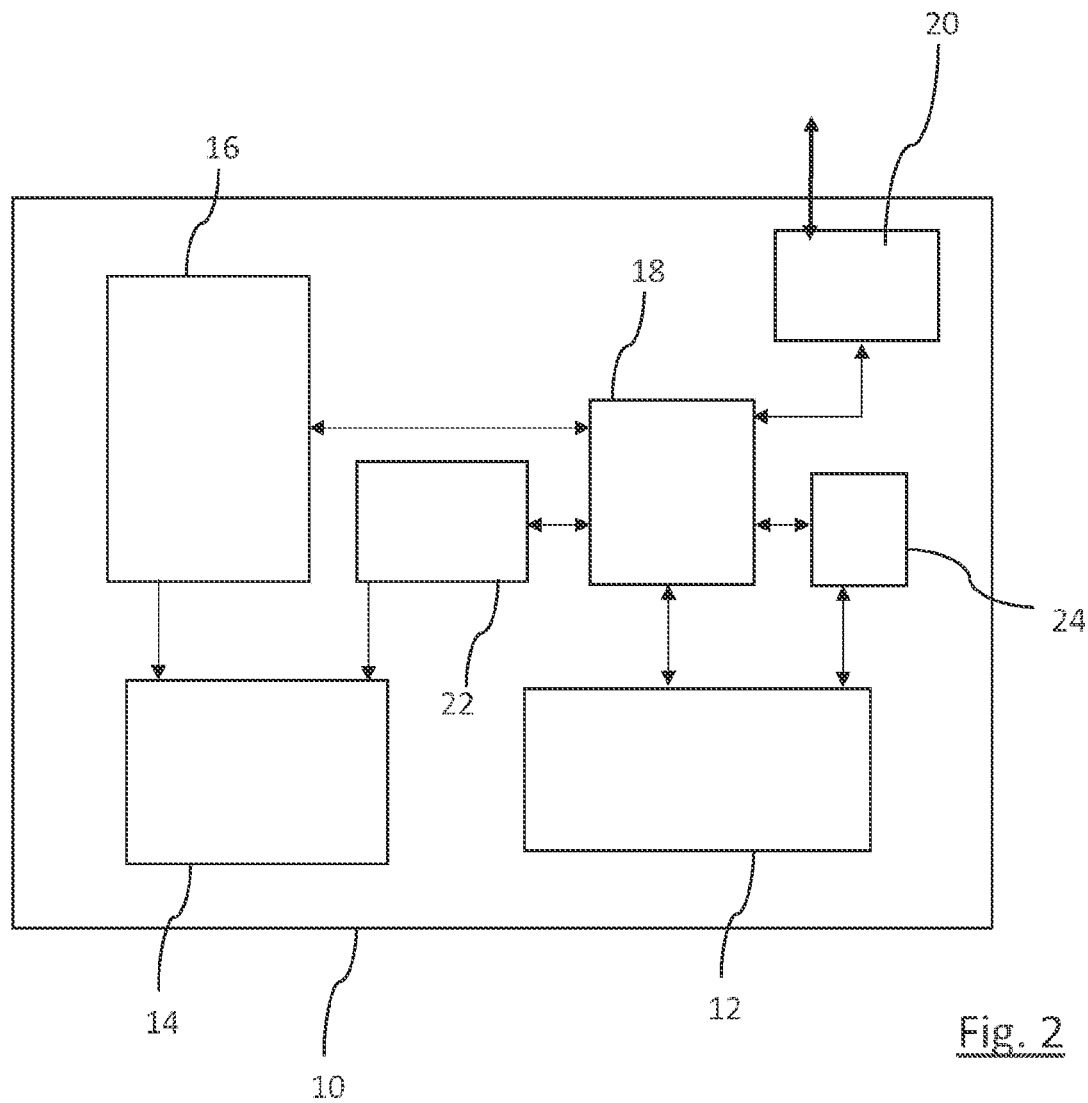
FIG. 2 shows a block diagram illustrating the various interacting components of the vending apparatus and FIG. 3 illustrates a flowchart executed by the vending apparatus during a typical vending procedure.

The schematic block diagram according to FIG. 2 illustrates interaction of the various components and modules of the vending apparatus 10. The vending apparatus 10 comprises input- and output means 12, an output or delivery module 14, a storage module 16, a central processing unit 18, a communication unit 20, a leaflet printing module 22 as well as an authorization module 24.

By means of the input-output means 12, a customer request is passed to the central processing unit 18. Depending on the type of request, the central processing unit 18 may interact with a communication unit 20 and/or with an authorization module 24 in order to check, if the customer is authorized to receive the requested medicinal product. By way of the communication unit 20, the vending apparatus 10 may for instance connect to a central database. Additionally or alternatively, the authorization module 24 may decode encrypted information provided by the customer in form of encrypted information on some kind of access medium, like a card medium.

Therefore, the input/output means may additionally comprise a card reader, adapted to read encoded customer-related information stored on a customer-card.

If the customer and/or the request have successfully passed the authorization step, the processing means 18 is adapted to at least display product- or medical device-related information via the input-output means 12. The input-output means 12 therefore comprise at least a screen and/or speakers for providing visual and/or audible product-related information. Providing of product-related information may be executed in an interactive way.

Hence, the customer may have to answer at least some selected product-related questions. If the customer fails to answer a predefined percentage of the questions, access to the requested product is denied and the vending procedure is subject to cancellation. In all other cases, where the customer correctly answers a number of product-related questions, the training procedure is successfully passed and the central processing unit 18 triggers printing of a requested leaflet by means of the leaflet printing module 22 and simultaneously triggers the storage module 16 to select and to hand out the product and/or the respective device to the customer by way of the output module 14.

Figure 3:
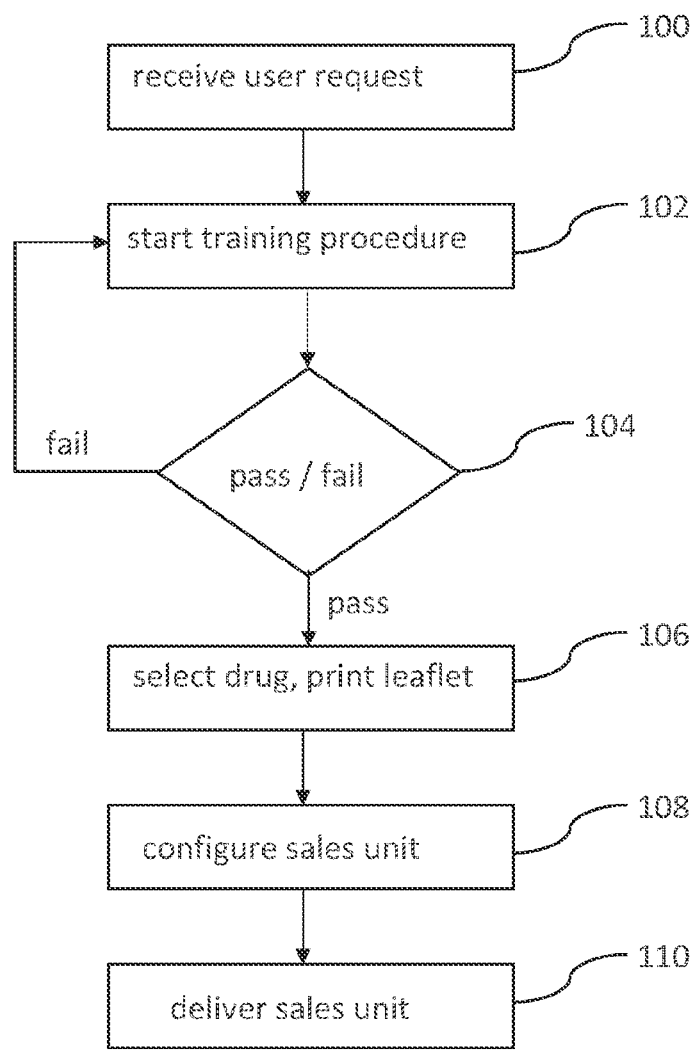

In FIG. 3, one possible vending procedure is schematically illustrated by way of a flowchart. In a first step 100, the customer requests a particular medicinal product and/or a medical device. Upon the request, the vending apparatus triggers a training procedure in step 102. In the training procedure, the customer has to answer essential product or device-related questions. If the customer fails in answering the product-related questions in step 104, the training procedure may be executed repeatedly and the procedure returns to step 102.

However, if the customer successfully passes the training procedure in step 104, the vending apparatus selects the requested drug and prints a respective language-specific leaflet in step 106.

In a further step 108, a sales unit comprising the product and/or the device together with the individually printed leaflet is configured and in a final step 110, the individually configured sales unit is handed out to the customer.

The invention claimed is:

1. A vending apparatus for at least one medicinal product, comprising:
   a housing,
   storage means adapted to store the at least one medicinal product,
   an input means adapted to process a costumer request for a medicinal product,
   processing means adapted to process the costumer request and being adapted to execute a product-related training procedure with the customer, and
   delivery means for handing out the medicinal product to the costumer after passing the training procedure, wherein
   access to the medicinal product is only approved by the processing means if the customer successfully passes the training procedure.

2. The apparatus according to claim 1, further comprising an authorization module for checking the identity of the customer and/or its authorization to receive the requested medicinal product.

3. The apparatus according to claim 1, wherein the storage module is adapted to be refrigerated.

4. The apparatus according to claim 1, further comprising a communication interface for communicating with a product-supply entity.

5. The apparatus according to claim 1, further comprising a leaflet printing module for printing of a customer-specific product-related leaflet.

6. The apparatus according to claim 1, wherein the input means comprises a touch-screen-display, a keypad and/or a speech dialog system.

7. A method of vending at least one medicinal product by means of an apparatus according to any one of the preceding claims, said method comprising the steps of:
   processing a costumer request for a medicinal product,
   selecting a product-related training procedure and executing said training procedure with the customer,
   providing access to the product and handing out the product to the customer after having successfully passed the training procedure.

8. The method according to claim 7, wherein the identity of the customer and/or its authorization to receive the requested medicinal product is checked prior to execution of the training procedure.

9. The method according to claim 7, wherein a product-related leaflet is printed on-site in response to a language selection of the costumer.

10. A computer program product for operating a vending apparatus according to claim 1, comprising:
    computer program means for processing a costumer request for a medicinal product,
    program means for selecting a product-related training procedure and executing said training procedure with the customer,
    program means for delivering the product to the customer after having successfully passed the training procedure.

* * * * *